United States Patent [19]

Kikuchi et al.

[11] Patent Number: 4,582,934
[45] Date of Patent: Apr. 15, 1986

[54] ALPHA,ALPHA-DIMETHYL-PHENYLACETANILIDE DERIVATIVES, PROCESS FOR PRODUCTION THEREOF, AND USE THEREOF AS INSECTICIDE

[75] Inventors: Yasuo Kikuchi; Kazuya Toda; Chiharu Morikawa, all of Nagano, Japan

[73] Assignee: Yashima Chemical Industrial Co., Ltd., Tokyo, Japan

[21] Appl. No.: 675,062

[22] Filed: Nov. 26, 1984

[30] Foreign Application Priority Data

Dec. 2, 1983 [JP] Japan ................... 58-227000

[51] Int. Cl.$^4$ ........................... C07C 103/22
[52] U.S. Cl. ........................ 564/182; 558/414
[58] Field of Search .................. 564/182; 260/465 E

[56] References Cited

U.S. PATENT DOCUMENTS 3,407,056 10/1968 Schwartz .......................... 564/182
4,453,975  6/1984 Takematsu et al. ............... 564/182

FOREIGN PATENT DOCUMENTS 76045  4/1984  Japan ............................ 564/182

Primary Examiner—Charles F. Warren
Assistant Examiner—R. A. Picard
Attorney, Agent, or Firm—Wenderoth, Lind & Ponack

[57] ABSTRACT

A compound of the general formula

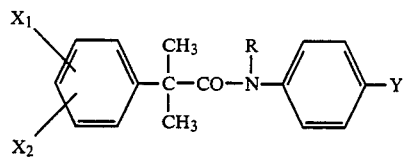

wherein $X_1$ represents a hydrogen, fluorine, chlorine or bromine atom, $X_2$ represents a fluorine, chlorine or bromine atom, R represents a hydrogen atom or a lower alkyl group, and Y represents a fluorine, chlorine or bromine atom, or a trifluoromethyl or cyano group.

This compound is prepared by reacting a compound of the formula

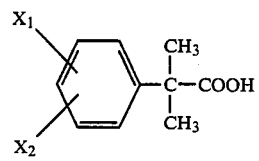

or a reactive derivative thereof with a compound of the formula

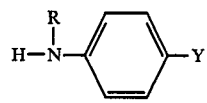

and is useful as an insecticide.

14 Claims, No Drawings

ALPHA,ALPHA-DIMETHYLPHENYLACETANILIDE DERIVATIVES, PROCESS FOR PRODUCTION THEREOF, AND USE THEREOF AS INSECTICIDE

This invention relates to novel phenylacetanilide derivatives. More specifically, it relates to alpha,alpha-dimethylphenylacetanilide derivatives represented by the following general formula

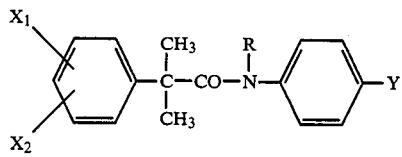

wherein $X_1$ represents a hydrogen, fluorine, chlorine or bromine atom, $X_2$ represents a fluorine, chlorine or bromine atom, R represents a hydrogen atom or a lower alkyl group, and Y represents a fluorine, chlorine or bromine atom, or a trifluoromethyl or cyano group, a process for production thereof, and to the use thereof as insecticides.

It has already been disclosed that phenylacetamide derivatives of a certain type have activity against mites parasitic on plants (see Japanese Laid-Open Patent Publication No. 35065/1980). U.S. Pat. No. 4,453,975 discloses that alpha,alpha-dimethylphenylacetanilide derivatives of a certain type have herbicidal activity.

We have synthesized many alpha,alpha-dimethylphenylacetanilide derivatives, and extensively studied their relation to their insecticidal effect. We have now surprisingly found that a specific group of novel alpha,alpha-dimethylphenylacetanilide derivatives represented by general formula (I) show a very high control effect against injurious insects which attack agricultural and horticultural crops, such as diamondback moth (*Plutella xylostella*) and *Thrips palmi*.

In the present specification and the appended claims, the term "lower" used to qualify a group or a compound means that the group or compound so qualified has not more than 6, preferably not more than 4, carbon atoms.

The "lower alkyl group" represented by R in formula (I) may be linear or branched, and includes, for example methyl, ethyl, n- or iso-propyl, n-, iso-, sec- or tert-butyl, pentyl and hexyl. Methyl and ethyl are preferred.

Compounds of formula (I) in which $X_1$ is a hydrogen atom and $X_2$ is a chlorine atom at the p-position are preferred. Among these components, those in which Y is a chlorine or bromine atom or a trifluoromethyl group are especially preferred.

Specific examples of the compounds of formula (I) which are considered desirable from the viewpoint of insecticidal activity are alpha,alpha-dimethyl-p-chlorophenylaceto-p-chloranilide, alpha,alpha-dimethyl-p-chlorophenylaceto-p-bromanilide, alpha,alpha-dimethyl-p-chlorophenylaceto-p-trifluoromethylanilide, alpha,alpha-dimethyl-p-chlorophenylaceto-N-ethyl-p-chloranilide, and alpha,alpha-dimethyl-p-chlorophenylaceto-N-ethyl-p-bromanilide.

According to this invention, the compound of formula (I) can be prepared, for example, by reacting a compound of the following formula

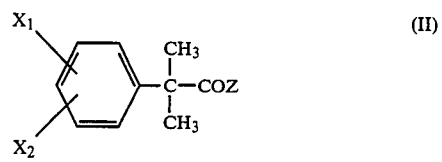

wherein $X_1$ and $X_2$ are as defined above, and Z represents a halogen atom, especially chlorine or bromine, a lower alkoxy group (e.g., methoxy or ethoxy), or a hydroxyl group, with an aniline derivative of the following formula

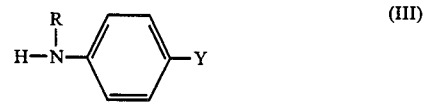

wherein R and Y are as defined above.

The reaction of the compound of formula (II) with the aniline derivative of formula (III) can be carried out in the absence of a solvent. Generally, however, it is carried out in an inert medium. Examples of the inert medium include aromatic hydrocarbons such as benzene, toluene and xylene, ethers such as diethyl ether, tetrahydrofuran and dioxane, alcohols such as methanol and ethanol, ketones such as acetone and methyl ethyl ketone, and halogenated hydrocarbons such as methylene chloride, chloroform and carbon tetrachloride. Benzene is especially suitable.

The reaction temperature is not critical, and can be varied widely depending upon the type of the starting materials and/or the solvent, etc. Generally, temperatures ranging from about 0° C. to the refluxing temperature of the reactant mixture, preferably about 20° C. to about 40° C., are advantageously used. The reaction pressure is usually atmospheric pressure, but as required, the reaction can be performed under reduced or elevated pressures.

The reaction can be carried out in the presence of general reaction aids. Examples of the reaction aids include alkali metal hydroxides such as sodium hydroxide, alkali metal carbonates such as sodium hydrogen carbonate, organic bases such as pyridine, triethylamine and tripropylamine, dicyclohexylcarbodiimide, phosphorus oxychloride, thionyl chloride, and phosphorus pentachloride. The amount of the reaction aids is desirably one equivalent to the compound of formula (II).

Advantageously, the aniline derivative of formula (III) is used in an amount of about one equivalent to the compound of formula (II).

Under the conditions described above, the reaction ends in about 0.5 to 10 hours. The recovery and purification of the desired compound of formula (I) from the reaction mixture may be carried out by methods known per se, for example by recrystallization (benzene, toluene, methanol, ethanol, chloroform, hexane, etc, are advantageous crystallization solvents), distillation, chromatography, etc.

The compounds of formula (II) used as a starting nmaterial in the above reaction, i.e. alpha,alpha-dimethylphenylacetic acid, alpha,alpha-dimethylphenylacetyl halides and alpha,alpha-dimethylphenylacetic acid esters, are known per se, or can be produced by methods known per se. For example, an alpha,alpha-dimethylphenylacetyl halide can be produced in a customary manner by reacting alpha,alpha-dimethylphenylacetic acid with a halogenating agent such as thionyl chloride, phosphorus trichloride, phosphorus tribromide or phosphorus pentachloride. An alpha,alpha-dimethylphenylacetic acid ester can be produced generally by dehydrocondensing alpha,alpha-dimethylphenylacetic acid with an alcohol such as methanol and ethanol.

The following Examples illustrate the production of the compound of formula (I) more specifically.

EXAMPLE 1

Production of compound No. 2

Benzene (50 ml), 0.64 g of p-chloraniline and 0.51 g of triethylamine were added to a 100 ml four-necked flask, and they were dissolved. To the solution was added dropwise 1.09 g of alpha,alpha-dimethyl-p-chlorophenylacetyl chloride with cooling and stirring. Then, the mixture was stirred at room temperature for 3 hours. After the reaction, the reaction mixture was poured into water to remove triethylamine hydrochloride. The benzene layer was dried over anhydrous sodium sulfate, and benzene was evaporated under reduced pressure. The residue was recrystallized from a mixture of hexane and ethyl acetate to give 1.3 g of alpha,alpha-dimethyl-p-chlorophenylaceto-p-chloranilide as a white solid.

Yield: 84.4%.
Melting point: 146°–147° C.
IR value $\nu$KBr/max: 1650 cm$^{-1}$ (—CO—), 3300 cm$^{-1}$ (—NH—).

EXAMPLE 2

Production of compound No. 10

Benzene (50 ml), 2.35 g of N-ethyl-p-bromoaniline and 1.2 g of triethylamine were added to a 100 ml four-necked flask, and they were dissolved. To the solution was added dropwise 2.55 g of alpha,alpha-dimethyl-p-chlorophenylacetyl chloride with cooling and stirring. Then, the mixture was stirred at room temperature for 10 hours. After the reaction, the reaction mixture was poured into water to remove triethylamine hydrochloride. The benzene layer was dried over anhydrous sodium sulfate, and benzene was evaporated under reduced pressure. The residue was purified by column chromatography using a 9:1 mixed solvent of n-hexane and ethyl acetate to give 3.6 g of alpha,alpha-dimethyl-p-chlorophenylaceto-N-ethyl-p-bromanilide as a colorless transparent liquid.

Yield: 80.5%.
N25/D: 1.5766.
IR $\nu$neat/max: 1640 cm$^{-1}$ (—CO—).

The compounds shown in Table 1 were obtained by operating in the same way as in Example 1 or 2.

TABLE 1

| Compound No. | Structural formula | Melting point (°C.) or refractive index ($n_D^{25}$) |
|---|---|---|
| 1 | Cl—C6H4—C(CH3)2—CONH—C6H4—F | 101–102 |
| 2 | Cl—C6H4—C(CH3)2—CONH—C6H4—Cl | 146–147 |
| 3 | Cl—C6H4—C(CH3)2—CONH—C6H4—Br | 145–147 |
| 4 | Cl—C6H4—C(CH3)2—CONH—C6H4—CF3 | 115–116 |
| 5 | Cl—C6H4—C(CH3)2—CONH—C6H4—CN | 130–131 |
| 6 | Cl—C6H4—C(CH3)2—CON(CH3)—C6H4—Cl | 93–94 |
| 7 | Cl—C6H4—C(CH3)2—CON(C2H5)—C6H4—Cl | 1.5688 |
| 8 | Cl—C6H4—C(CH3)2—CON(nC3H7)—C6H4—Cl | 1.5564 |
| 9 | Cl—C6H4—C(CH3)2—CON(nC4H9)—C6H4—Cl | 113–114 |
| 10 | Cl—C6H4—C(CH3)2—CON(C2H5)—C6H4—Br | 1.5766 |
| 11 | F—C6H4—C(CH3)2—CONH—C6H4—Cl | 98–99 |
| 12 | F—C6H4—C(CH3)2—CONH—C6H4—CF3 | 94–96 |
| 13 | F—C6H4—C(CH3)2—CON(C2H5)—C6H4—Cl | 85–86 |
| 14 | F—C6H4—C(CH3)2—CON(C2H5)—C6H4—Br | 103.5–104.5 |
| 15 | Br—C6H4—C(CH3)2—CONH—C6H4—Cl | 163–164 |

TABLE 1-continued

| Compound No. | Structural formula | Melting point (°C.) or refractive index ($n_D^{25}$) |
|---|---|---|
| 16 | 2-F-C$_6$H$_4$-C(CH$_3$)$_2$-CONH-C$_6$H$_4$-4-Cl | 113–114 |
| 17 | 2-F-C$_6$H$_4$-C(CH$_3$)$_2$-CONH-C$_6$H$_4$-4-CF$_3$ | 99–101 |
| 18 | 2-F-C$_6$H$_4$-C(CH$_3$)$_2$-CON(CH$_3$)-C$_6$H$_4$-4-Cl | 1.5573 |
| 19 | 2,4-Cl$_2$-C$_6$H$_3$-C(CH$_3$)$_2$-CONH-C$_6$H$_4$-4-Cl | 111–113 |
| 20 | 2,4-Cl$_2$-C$_6$H$_3$-C(CH$_3$)$_2$-CONH-C$_6$H$_4$-4-F | 90–92 |

The compounds of formula (I) provided by this invention show strong and wide insecticidal activity with little phytotoxicity on agricultural and horticultural crops (with a large tolerance), and are useful as an active ingredient of an agricultural and horticultural insecticide. The active compounds of formula (I) in accordance with this invention are expected to exhibit an excellent control efficacy against imagoes as well as larvae of insects which attack agricultural and horticultural crops. Examples of such insects include lepidopterous insects such as *Plutella xylostella, Carposina niponensis, Grapholita molesta, Adoxophyes orana, Adoxophyes* sp., *Chilo suppressalis* and *Pieris rapae crucivora*; thysanopterous insects such as *Thrips palmi, Scirtothrips dorsalis* and *Frankliniella intonsa*; coleopterous insects such as *Lissorhoptrus oryzophilus, Echinocnemus squameus, Phyllotreta striolate* and *Oulema oryzae*; and dipterous insects such as *Hylemya platura* and *Asphondylia* sp.

It should be understood that the term "insecticidal", as used in the present specification and the appended claims, means killing insects both in the stages of larvae and imagoes.

Particularly, the compounds of this invention represented by formula (I) shows excellent insecticidal activity against diamondback moth (*Plutella xylostella*) which is designated in Japan as one of difficult-to-control injurious insects and causes hazards to agricurture and horticulture. It also shows a very high control efficacy against thrips such as *Thrips palmi* which occurred in Japan in 1978 as new injurious insect and are most important injurious insects against fruits and vegetables mainly in the western part of Japan.

Accordingly, the active compound of formula (I) in accordance with this invention is useful as an active ingredient of an agricultural and horticultural insecticide. When the compound of formula (I) is to be actually applied as an active ingredient of an insecticide, it can be formulated into an insecticidal composition suitable for the application by incorporating agriculturally and horticulturally acceptable carriers or diluents.

Examples of the carrier or diluents include solid carriers such as kaolin, talc, clay, diatomaceous earth, white carbon, alumina, quartz, attapulgite, montmorillonite and silica; liquid carriers or diluents such as water, xylene, toluene, benzene, methylnaphthalene, chlorobenzene, chloroethylene, methylene chloride, cyclohexane, mineral oil fractions, alcohols, glycols, ethers, esters, ketones (e.g., acetone, methyl ethyl ketone, methyl isobutyl ketone, and cyclohexanone), dimethylformamide and dimethyl sulfoxide; and liquefied products of normally gaseous substances, such as propane, butane and Freon.

As required, the insecticidal composition of this invention includes emulsifiers such as nonionic polyoxyalkylene alkyl ethers, polyoxyalkylene alkyl aryl ethers, polyoxyalkylene fatty acid esters and polyoxyalkylene sorbitan fatty acid esters, and anionic alkylaryl sulfuric acids ester salts, polyoxyalkylene alkylaryl sulfuric acid ester salts and polyoxyalkylene alkyl aryl phosphoric acid ester salts; and mixtures of the above-types of emulsifiers; dispersants such as ligninsulfonic acid salts, methyl cellulose alkyl sulfuric acid ester salts, alkylbenzenesulfonic acid salts, dialkylsulfosuccinic acid ester salts, naphthalenesulfonic acid/formaldehyde condensate, polyoxyalkylene alkyl sulfuric acid ester salts, and mixtures of the above compounds; and stabilizers such as phosphoric acid esters, epichlorohydrin, phenyl glycidyl ether, glycols, nonionic surface-active agents and aromatic diamines. In some cases, it is possible to incorporate adhesives (e.g., carboxymethyl cellulose, gum arabic, polyvinyl alcohol and polyvinyl acetate) and coloring agents (various pigments and dyes).

Furthermore, the insecticidal composition of this invention may contain other active compounds, for example compounds having insecticidal, miticidal, fungicidal and herbicidal activities, as is frequently the case in the art. They include, for example, insecticides such as Fenitrothion [O,O-dimethyl O-(3-methyl-4-nitrophenyl) phosphorothioate], Diazinon {O,O-diethyl O-[6-methyl-2-(1-methylethyl)-4-pyrimidinyl]phosphorothioate} and NAC (1-napthalenyl methylcarbamate); miticides such as Dicofol [4-chloro-alpha-(4-chlorophenyl)-alpha-(trichloromethyl)benzenemethanol] and Cyhexatin (tricyclohexylhydroxystannane); fungicides such as Kasugamycin {D-3-O-[2-amino-4-[(1-carboxyiminomethyl)amino]-2,3,4,6-tetradeoxy-alpha-D-arabinohexopyranosyl]-D-chiro-inositol}, Polyoxin {5-[[2-amino-5-O-(aminocarbonyl)-2-deoxy-L-xylonyl]amino]-1,5-dideoxy-1-[3,4-dihydro-5-(hydroxymethyl)-2,4-dioxo-1(2H)-pyrimidinyl]-beta-D-allofuranuronic acid} and Zineb {[[1,2-ethanediynl bis[carbamodithioate]](2-)]zinc complex}; and herbicides such as Carbodimedon [2-(1-allyloxyaminobutylidene)-5,5-dimethyl-4-methoxycarbonylcyclohexane-1,3-dione, Na salt], Simazine (2-chloro-N,N'-diethyl-1,3,5-triazine-4,6-diamine) and Alachlor [2-chloro-N-(2,6-diethylphenyl)-N-(methoxymethyl)acetamide].

By using the aforesaid mixing components, the insecticidal composition of this invention can be formulated by methods known per se into liquid preparations, emulsifiable concentrates, wettable powders, dusts, fine particles, granules, aerosols, etc. The concentration of the active compound in the composition can be varied widely according to the form of the composition, the type of the active compound, etc. Generally, concentrations in the range of 0.5 to 80% by weight based on the weight of the composition are suitable. Preferably, according to the form of the composition, for example in the case of liquid preparations, emulsifiable concentrates and wettable powders, the compound of formula (I) may be incorporated in a concentration of 10 to 80% by weight, preferably 30 to 70% by weight. In the case of dusts, fine particles and granules, the compound of formula (I) may be included in a concentration of 0.5 to 30% by weight, preferably 2 to 20% by weight.

The insecticide or insecticidal composition of this invention can be used to combat injurious insects by applying it in an amount sufficient to provide an insecticidally effective amount of the compound of formula (I) to insects (imagoes or larvae) injurious to agricultural and horticultural crops or to their habitat. The dosage of the compound of formula (I) in this case may be widely changed depending upon the type of the active compound, or the form of the insecticide or insecticidal composition. In the case of emulsifiable concentrates, liquid preparations and wettable powders, they can usually be diluted to 1,000 to 10,000 times and sprayed at a rate of 100 to 1,000 liters per 10 ares. The suitable rate of application of dusts, fine particles or granules may usually be 2 to 5 kg/10 ares.

The following Formulation Examples illustrate the formulation of the insecticidal composition of this invention. All parts in these examples are by weight.

| Formulation Example 1 | |
|---|---|
| Dust: | |
| Compound No. 3 | 3 parts |
| Talc | 30 parts |
| Clay | 66.7 parts |
| Isopropyl phosphate | 0.3 part |

The above ingredients are mixed and pulverized to obtain 100 parts of a dust.

| Formulation Example 2 | |
|---|---|
| Wettable powder: | |
| Compound No. 4 | 50 parts |
| Sodium ligninsulfonate | 3 parts |
| Sodium alkylbenzenesulfonate | 2 parts |
| White Carbon | 10 parts |
| Diatomaceous earth | 35 parts |

The above ingredients are mixed and pulverized to obtain 100 parts of a wettable powder.

| Formulation Example 3 | |
|---|---|
| Emulsifiable concentrate: | |
| Compound No. 7 | 50 parts |
| Polyoxyethylene alkylaryl ether | 12 parts |
| Polyoxyethylene alkyl sulfate | 3 parts |
| Xylene | 35 parts |

The above ingredients are mixed to form 100 parts of an emulsifiable concentrate.

The following Test Examples demonstrate the superior insecticidal effect of the active compound of formula (I) in accordance with this invention.

Test Example 1

Indoor test on 3rd-instar larvae of *Plutella xylostella*:

A wettable powder prepared as in Formulation Example 2 was diluted to a predetermined concentration. Cabbage leaves were dipped for 10 seconds in the resulting dilution and then air dried. The leaves were put into a polyvinyl chloride cup having a capacity of 90 ml together with 3rd-instar larvae of *Plutella xylostella*. The cup was left to stand in a constant temperature chamber kept at 25° C., and 72 hours later, the number of dead insects was examined. For each test area, the test was repeated twice, and 20 insects were used in each area. The ratio of the dead insects was calculated, and $LC_{50}$ (50% lethal concentration) values of the test compounds were determined by the method of Bliss. The results are shown in Table 2.

The sensitive *Plutella xylostella* insects in the table were those bred through generations at the Laboratory of Yashima Chemical Industrial Co., Ltd. The resistant ones were hunted at Tsumakoi-mura, Gunma-ken, Japan.

TABLE 2

| Compound No. | Sensitive *Plutella xylostella* $LC_{50}$ (ppm) | Resistant *plutella xylostella* $LC_{50}$ (ppm) |
|---|---|---|
| 1 | 126 | 123 |
| 2 | 101 | 110 |
| 3 | 57 | 51 |
| 4 | 95 | 96 |
| 5 | 97 | 90 |
| 6 | 61 | 60 |
| 7 | 51 | 53 |
| 8 | 198 | 204 |
| 9 | 372 | 365 |
| 10 | 48 | 46 |
| 11 | 107 | 111 |
| 12 | 95 | 110 |
| 13 | 74 | 73 |
| 14 | 88 | 93 |
| 15 | 137 | 129 |
| 16 | 320 | 331 |
| 17 | 281 | 256 |
| 18 | 213 | 211 |
| 19 | 119 | 106 |
| 20 | 122 | 128 |
| DDVP[*1] | 103 | 1020 |
| Acephate[*2] | 178 | 878 |

[*1] 2,2-dichlorovinyl dimethyl phosphate
[*2] O,S—dimethyl N—acetylphosphoramidothiolate Test Example 2

Field test on *Plutella xylostella*:

A wettable powder produced in accordance with Formulation Example 2 was diluted to a predetermined concentration, and the dilution was sprayed in an amount of 500 liters/10 areas onto cabbage on which resistant *Plutella xylostella* lived by using a powered sprayer. On predetermined dates, the number of larvae per 10 heads of cabbage was examined, and the corrected density indices of the test compounds were calculated in accordance with the following equation.

$$\text{Corrected density index} = \frac{\begin{pmatrix}\text{number of insects in the non-treated area before the test}\end{pmatrix} \times \begin{pmatrix}\text{number of insects in the treated area after the test}\end{pmatrix}}{\begin{pmatrix}\text{number of insects in the non-treated area after the test}\end{pmatrix} \times \begin{pmatrix}\text{number of insects in the treated area before the test}\end{pmatrix}} \times 100$$

The results are shown in Table 3.

TABLE 3

| Compound No. | Concentration (ppm) | Corrected density index | | |
|---|---|---|---|---|
| | | After 3 days | After 7 days | After 14 days |
| 2 | 250 | 10 | 5 | 2 |
| 3 | 250 | 7 | 2 | 3 |
| 4 | 250 | 7 | 1 | 0 |
| 7 | 250 | 4 | 0 | 0 |
| 10 | 250 | 5 | 0 | 0 |
| DDVP*[1] | 500 | 15 | 52 | 86 |
| Acephate*[2] | 500 | 8 | 12 | 15 |
| Not sprayed | — | 100 | 100 | 100 |

*[1] and *[2] Same as the footnote to Table 2.

Test Example 3

Test on *Thrips palmi:*

An emulsifiable emulsion prepared as in Formulation Example 3 was diluted with water to a predetermined concentration. The dilution was sprayed on eggplants which were grown in pots and on which *Thrips palmi* was parasitic, so that the dilution fully dripped on the plant leaves. The number of dead insects was examined at predetermined dates, and the corrected density indices of the test compounds were calculated. For each area, the test was repeated three times. The results are shown in Table 4.

TABLE 4

| Compound No. | Concentration (ppm) | Corrected density index | | |
|---|---|---|---|---|
| | | After 1 day | After 3 days | After 7 days |
| 2 | 500 | 20 | 10 | 12 |
| | 250 | 16 | 14 | 14 |
| 3 | 500 | 9 | 3 | 3 |
| | 250 | 16 | 8 | 14 |
| 4 | 500 | 12 | 4 | 6 |
| | 250 | 19 | 8 | 11 |
| 7 | 500 | 10 | 2 | 3 |
| | 250 | 16 | 9 | 13 |
| 10 | 500 | 7 | 1 | 4 |
| | 250 | 12 | 12 | 11 |
| BPMC*[3] | 500 | 2 | 15 | 45 |
| | 250 | 7 | 35 | 57 |
| Not sprayed | — | 100 | 100 | 100 |

*[3] 2-sec. butylphenyl-N—methyl carbamate

What is claimed is:

1. A compound of the general formula $$\underset{X_2}{\overset{X_1}{\phantom{X}}}\!\!-\!\!\underset{CH_3}{\overset{CH_3}{\underset{|}{\overset{|}{C}}}}\!\!-\!\!CO\!\!-\!\!\underset{}{\overset{R}{\underset{|}{N}}}\!\!-\!\!\bigcirc\!\!-\!\!Y \quad (I)$$

wherein $X_1$ represents a hydrogen, fluorine, chlorine or bromine atom, $X_2$ represents a fluorine, chlorine or bromine atom, R represents a hydrogen atom or a lower alkyl group, and Y represents a fluorine, chlorine or bromine atom, or a trifluoromethyl or cyano group.

2. The compound of claim 1 wherein $X_1$ is a hydrogen atom and $X_2$ represents a chlorine atom at the p-position.

3. The compound of claim 2 wherein Y is a chlorine or bromine atom or a trifluoromethyl or cyano group.

4. The compound of claim 1 which is selected from the group consisting of alpha,alpha-dimethyl-p-chlorophenylaceto-p-chloranilide, alpha,alpha-dimethyl-p-chlorophenylaceto-p-bromanilide, alpha,alpha-dimethyl-p-chlorophenylaceto-p-trifluoromethylanilide, alpha,alpha-dimethyl-p-chlorophenylaceto-N-ethyl-p-chloranilide, and alpha,alpha-dimethyl-p-chlorophenylaceto-N-ethyl-p-bromanilide.

5. An insecticide comprising as an active ingredient a compound of the general formula $$\underset{X_2}{\overset{X_1}{\phantom{X}}}\!\!-\!\!\underset{CH_3}{\overset{CH_3}{\underset{|}{\overset{|}{C}}}}\!\!-\!\!CO\!\!-\!\!\underset{}{\overset{R}{\underset{|}{N}}}\!\!-\!\!\bigcirc\!\!-\!\!Y \quad (I)$$

wherein $X_1$ represents a hydrogen, fluorine, chlorine or bromine atom, $X_2$ represents a fluorine, chlorine or bromine atom, R represents a hydrogen atom or a lower alkyl group, and Y represents a fluorine, chlorine or bromine atom, or a trifluoromethyl or cyano group.

6. The insecticide of claim 5 wherein $X_1$ is a hydogen atom and $X_2$ represents a chlorine atom at the p-position.

7. The insecticide of claim 6 wherein Y is a chlorine or bromine atom or a trifluoromethyl or cyano group.

8. The insecticide of claim 5 wherein the active ingredient is selected from the group consisting of alpha,alpha-dimethyl-p-chlorophenylaceto-p-chloranilide, alpha,alpha-dimethyl-p-chlorophenylaceto-p-bromanilide, alpha,alpha-dimethyl-p-chlorophenylaceto-p-trifluoromethylanilide, alpha,alpha-dimethyl-p-chlorophenylaceto-N-ethyl-p-chloranilide, and alpha,alpha-dimethyl-p-chlorophenylaceto-N-ethyl-p-bromanilide.

9. An insecticidal composition comprising an insecticidally effective amount of a compound of the general formula $$\underset{X_2}{\overset{X_1}{\phantom{X}}}\!\!-\!\!\underset{CH_3}{\overset{CH_3}{\underset{|}{\overset{|}{C}}}}\!\!-\!\!CO\!\!-\!\!\underset{}{\overset{R}{\underset{|}{N}}}\!\!-\!\!\bigcirc\!\!-\!\!Y \quad (I)$$

wherein $X_1$ represents a hydrogen, fluorine, chlorine or bromine atom, $X_2$ represents a fluorine, chlorine or bromine atom, R represents a hydrogen atom or a lower alkyl group, and Y represents a fluorine, chlorine or bromine atom, or a trifluoromethyl or cyano group,
and an agriculturally and horticulturally acceptable carrier or diluent.

10. The composition of claim 9 wherein $X_1$ is a hydrogen atom and $X_2$ represents a chlorine atom at the p-position.

11. The composition of claim 10 wherein Y is a chlorine or bromine atom or a trifluoromethyl or cyano group.

12. The composition of claim 9 wherein said compound is selected from the from the group consisting of alpha,alpha-dimethyl-p-chlorophenylaceto-p-chloranilide, alpha,alpha-dimethyl-p-chlorophenylaceto-p-bromanilide, alpha,alpha-dimethyl-p-chlorophenylaceto-p-trifluoromethylanilide, alpha,alpha-dimethyl-p-chlorophenylaceto-N-ethyl-p-chloranilide, and alpha,alpha-dimethyl-p-chlorophenylaceto-N-ethyl-p-bromanilide.

13. The composition of claim 9 which contains the compound of formula (I) in a concentration of 0.5 to 80% by weight.

14. The composition of claim 9 which is in the form of a dust, a wettable powder or an emulsifiable concentrate.

* * * * *